US00PP31126P2

(12) United States Plant Patent
Hansen

(10) Patent No.: US PP31,126 P2
(45) Date of Patent: Nov. 26, 2019

(54) ***ALLIUM* PLANT NAMED 'LAVENDER BUBBLES'**

(50) Latin Name: ***Allium* hybrid (Linnaeus)**
Varietal Denomination: Lavender Bubbles

(71) Applicant: Hans A Hansen, Zeeland, MI (US)

(72) Inventor: Hans A Hansen, Zeeland, MI (US)

(73) Assignee: Walters Garden Inc, Zeeland, MI (US)

( * ) Notice: Subject to any disclaimer, the term of this patent is extended or adjusted under 35 U.S.C. 154(b) by 0 days.

(21) Appl. No.: 16/350,924

(22) Filed: Feb. 1, 2019

(51) Int. Cl.
*A01H 5/02* (2018.01)
*A01H 6/04* (2018.01)

(52) U.S. Cl.
USPC ..... Plt./263.1

(58) Field of Classification Search
USPC ..... Plt./263.1
See application file for complete search history.

*Primary Examiner* — Susan McCormick Ewoldt
*Assistant Examiner* — Karen M Redden

(57) ABSTRACT

A new and distinct cultivar of ornamental onion plant named *Allium* 'Lavender Bubbles' compact habit, glaucous, upright, stiff, strap-like, flattened, gray-green foliage with slight longitudinal twisting and numerous, tightly-clustered, dark dusty-purple flowers forming in globose umbels.

1 Drawing Sheet

Botanical classification: *Allium* hybrid (Linnaeus).
Variety denomination: 'Lavender Bubbles'.

STATEMENT REGARDING PRIOR DISCLOSURES UNDER 37 CFR 1.77(B)(6)

The first public disclosure of the claimed plant, in the form of a photograph and brief description on a website operated by Walters Gardens, Inc. on Feb. 1, 2018. The claimed plant was first sold on Sep. 24, 2018 by Walters Gardens, Inc., who obtained the plant and all information relating thereto, from the inventor. No plants of *Allium* 'Lavender Bubbles' have been sold in this country or anywhere in the world, nor has any disclosure of the new plant been made, more than one year prior to the filing date of this application, and such sale or disclosure within one year was either derived directly or indirectly from the inventor.

BACKGROUND AND ORIGIN OF THE PLANT

The present invention relates to the new and distinct ornamental onion, *Allium* 'Lavender Bubbles' was developed by the inventor at a wholesale perennial nursery in Zeeland, Mich., USA as the result of self-pollination of proprietary unreleased selection known as H9-09-01 (not patented) in August of 2011. Seeds from this pollination were collected in fall of 2011 and were sown later that same year. The plant was originally selected in the summer of 2013 and given the breeder code 11-1-1.

*Allium* 'Lavender Bubbles' has been successfully asexually propagated by garden bulb division method since 2013 at a wholesale perennial nursery in Zeeland, Mich. and found to be stable and produce identical plants that maintain the unique characteristics of the original plant through multiple generations.

SUMMARY OF THE PLANT

*Allium* 'Lavender Bubbles' differs from its parents as well as all other ornamental onion known to the applicant. The most similar known *Allium* cultivars are 'Medusa' U.S. Plant Pat. No. 28,701, 'Blue Eddy' (not patented), *Allium tanguticum* 'Summer Beauty' (not patented), and 'Millenium' (not patented). 'Blue Eddy' has shorter and more twisted leaves, flowers and overall habit and smaller flower globes and lighter colored flowers. 'Summer Beauty' has less glaucous foliage, lighter flowers in larger umbels and produces no seed. 'Millenium' has lighter purple flowers beginning about three weeks earlier than the new plant, and also has darker green leaves. The female parent has more twisted foliage than the new plant with lighter purple flowers.

*Allium* 'Lavender Bubbles' differs from these above cultivars and all unregistered cultivars known to the inventor in that it has:

1. Glaucous, upright, stiff, strap-like, flattened, gray-green foliage with slight longitudinal twisting;
2. Compact habit, drought tolerant, rabbit and deer resistant, medium-sized clumps;
3. Numerous, tightly-clustered, dark dusty-purple flowers forming dense globose umbel;
4. Strong stems hold flowers heads upright through flowering and seed production.

BRIEF DESCRIPTION OF THE DRAWINGS

The photographs of the new plant demonstrate the overall appearance of the plant, including the unique traits. The colors are as accurate as reasonably possible with color reproductions. Ambient light spectrum, source and direction may cause the appearance of minor variation in color.

DETAILED BOTANICAL DESCRIPTION

Figure 1:
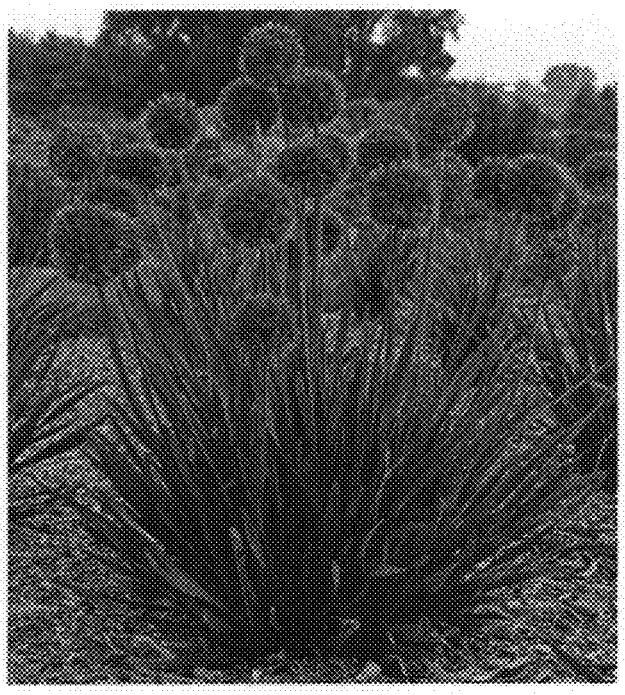
FIG. 1 shows the side-view habit of a three-year-old plant in early flowering.
Figure 2:
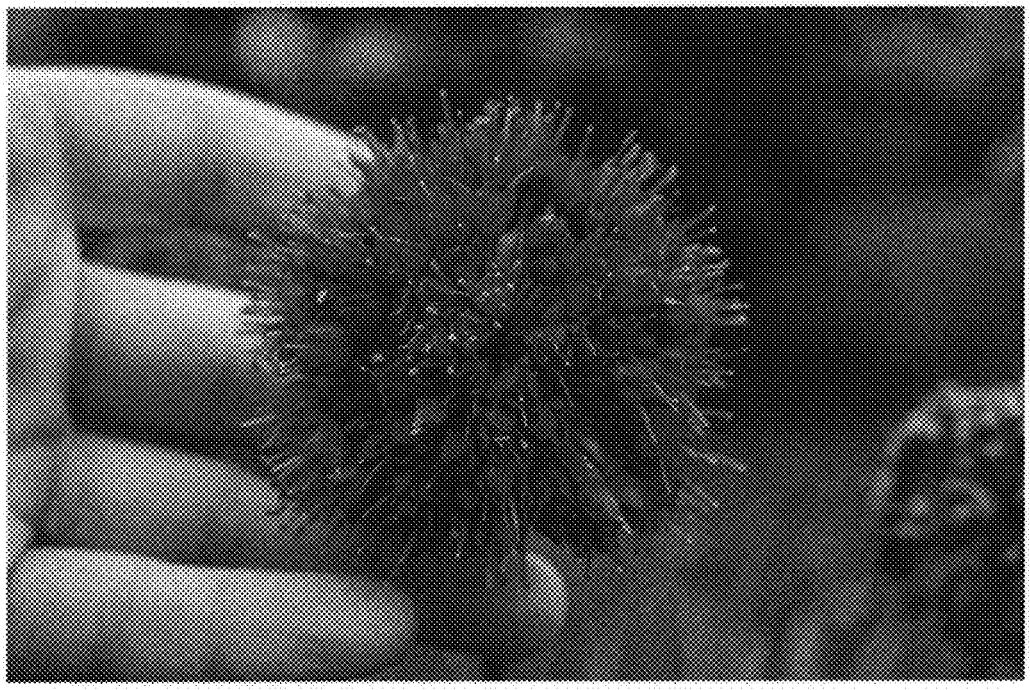
FIG. 2 shows a close-up of the umbel with flowers and buds.

The following descriptions and color references are based on the 2015 edition of The Royal Horticultural Society Colour Chart except where common dictionary terms are used. The new plant, *Allium* 'Lavender Bubbles', has not been observed under all possible environments. The phenotype may vary slightly with different environmental conditions, such as temperature, light, fertility, moisture and maturity levels, but without any change in the genotype. The following observations and size descriptions are of a three-year-old plant in a trial garden of a wholesale perennial nursery in Zeeland, Mich. under full sun with supplemental water and fertilizer as needed.

Botanical classification: *Allium* hybrid;

Parentage: Self-pollination of H9-09-01, which is selection from the cross between a proprietary seedling of 'Millenium' times a different unnamed proprietary seedling selection of 'Millenium';

Propagation method: By garden bulb division;

Growth rate: Vigorous, flowering in 4 liter containers in about 12 weeks;

Rooting habit: Fibrous from base of bulbs, lightly branching; color nearest RHS 158C;

Plant habit description: Dense clump of bulbs with sessile rosulate foliage about 70.0 cm across and about 45.0 cm tall; flowering to about 61.0 cm tall;

Bulbs: Elongated conical shape; about 6.5 cm long and 1.5 cm diameter at base; about 30 per plant; color nearest RHS 155D;

Leaves: Sessile; linear; glaucous, glabrous dull surfaces; semi-succulent; simple, margin entire; sharply acute apex, truncate base; slightly twisted longitudinally 180°; mostly flat; about 45.0 cm long and about 12.0 mm diameter at base; arranged in two-ranked tuffs from bulb; fragrance onion-scented;

Leaf color: Mature and expanding leaves same; both surfaces nearest RHS N138B distally with base nearest RHS 146D;

Leaf venation: Parallel; color same as leaf abaxial and adaxial;

Inflorescence: In terminal umbel; about 250 to 300 flowers per inflorescence; about 31 inflorescences per plant; globose, about 9.0 cm across and about 8.5 cm tall; lasting about three weeks; onion-like fragrance; beginning in mid to late-August in Michigan and continuing for three weeks;

Blooming habit: With upright globe in bud, remaining upright as initial flowers open; one terminal umbel inflorescence per stem;

Flowers: Campanulate; incomplete; perfect; with two sets of three tepals, outer set smaller than inner; inferior ovary; actinomorphic; upward and outwardly facing depending on position in umbel; individually effective about four to six days; from base to exerted stamens to about 12.0 mm long and about 7.0 mm across;

Tepals (outer set): Ovate to deltoid; convex; glabrous; lustrous; acute apex, fused truncate base; about 5.0 mm long and about 2.5 m across;

Tepal (inner set): Ovate to deltoid; flat; glabrous; lustrous; acute apex, broadly acute base; about 6.5 mm long and about 3.0 mm across;

Tepal color (inner and outer sets identical): Adaxial apex between RHS N77B and RHS N77C, abaxial between RHS N77B and RHS N77D;

Buds one day prior to opening: Globose to pyramidal, with three flattened sides; rounded base, rounded apex; about 6.0 mm long and about 5.0 mm diameter at widest point; Bud color: between RHS N77B and N79D;

Pedicel: Cylindrical; stiff, upward and outwardly facing depending on orientation in umbel; glabrous; glaucous; about 19.0 mm long and about 1.0 mm diameter;

Pedicel color: Nearest RHS 138A;

Peduncle: Glabrous, glaucous; flattened trapezoid in cross-section; about 60.0 cm long, base about 9.0 mm wide and about 7.0 mm thick;

Peduncle color: Base nearest RHS N138D, upper region between RHS N138B and RHS 189A;

Gynoecium: Pistil single; to about 8.0 mm long;

*Style*.—Single, cylindrical, glabrous, about 2.5 long expanding to 4.5 mm long and about 0.5 mm across when mature; color initially nearest RHS 77D or lighter becoming nearest RHS 77A.

*Stigma*.—Globose; about 0.2 mm across; color lighter than RHS 76D.

*Ovary*.—Distinctly tri-loculed; obcordate, widest at apex and narrowest at base; about 3.0 mm long and 4.0 mm across at acute apex and 3.0 mm across at truncate base; color nearest RHS 77C at base.

Androecium: Six; exserted to about 9.5 mm long;

*Anther*.—Oblong; about 2.0 mm long and about 0.7 mm wide; basifixed; longitudinal; color between RHS 177A and RHS N187B.

*Filament*.—Exserted; glabrous; cylindrical; about 8.0 mm long and 1.0 mm at base; color nearest RHS 77A at apex and lightening to nearest RHS NN155D at base.

*Pollen*.—Abundant; color nearest RHS 158B.

Fruit: Tri-valved loculicidal capsule; about 6.0 mm long and 4.5 mm across; typically dehiscing to within about 1.0 mm of base; one to three seeded; color upon maturity nearest RHS 199D;

Seed: Elliptic, flattened along one long side; about 2.5 mm long and about 1.5 mm across; color nearest RHS 202A;

Disease and pest resistance: Ornamental onions typically resist deer and rabbit feeding. Resistance beyond that of other ornamental onion has not been observed. *Allium* 'Lavender Bubbles' plant grows best with good drainage and is able to tolerate some drought when established. Hardiness at least from USDA zone 4 through 8.

I claim:

1. A new and distinct cultivar of ornamental onion plant named *Allium* 'Lavender Bubbles' as herein described and illustrated.

* * * * *